United States Patent [19]

Haga et al.

[11] Patent Number: 4,720,297
[45] Date of Patent: Jan. 19, 1988

[54] BENZOTHIAZOLONES, AND THEIR PRODUCTION AND USE AS HERBICIDES

[75] Inventors: Toru Haga, Takarazuka; Eiki Nagano, Nishinomiya; Ryo Sato; Kouichi Morita, both of Toyonaka, all of Japan

[73] Assignee: Sumitomo Chemical Company, Limited, Osaka, Japan

[21] Appl. No.: 911,360

[22] Filed: Sep. 25, 1986

[30] Foreign Application Priority Data

| Sep. 27, 1985 | [JP] | Japan | 60-216043 |
|---|---|---|---|
| Dec. 5, 1985 | [JP] | Japan | 60-274113 |
| Dec. 5, 1985 | [JP] | Japan | 60-274114 |
| Dec. 5, 1985 | [JP] | Japan | 60-274115 |
| Jan. 6, 1986 | [JP] | Japan | 61-001171 |

[51] Int. Cl.$^4$ .................... A01N 43/78; C07D 277/68
[52] U.S. Cl. .................... 71/90; 548/159; 548/161; 548/164
[58] Field of Search .................... 71/90; 548/159

[56] References Cited

U.S. PATENT DOCUMENTS

| Re. 31,068 | 10/1982 | D'Amico | 71/90 |
|---|---|---|---|
| 4,319,914 | 3/1982 | Stach | 71/90 |
| 4,420,327 | 12/1983 | Jikihara et al. | 548/513 |
| 4,439,229 | 3/1984 | Smithenbank | 548/513 |
| 4,556,411 | 12/1985 | Baum et al. | 71/90 |
| 4,577,029 | 3/1986 | Aoki et al. | 71/90 |
| 4,640,707 | 2/1987 | Nagano et al. | 71/96 |

FOREIGN PATENT DOCUMENTS 126419 11/1984 European Pat. Off.

*Primary Examiner*—Mary E. Ceperley
*Attorney, Agent, or Firm*—Birch, Stewart, Kolasch and Birch

[57] ABSTRACT

A compound of the formula:

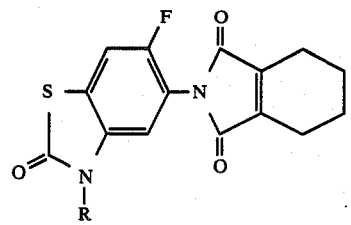

wherein R is a hydrogen atom, a $C_1$–$C_5$ alkyl group, a $C_3$–$C_4$ alkenyl group, a $C_3$–$C_4$ alkynyl group, a halo($C_1$–$C_4$)alkyl group, a halo($C_3$–$C_4$)alkenyl group, a halo($C_3$–$C_4$)alkynyl group, a $C_1$–$C_2$ alkoxy($C_1$–$C_2$)alkyl group, a $C_1$–$C_2$ alkoxy($C_1$–$C_2$)alkoxy($C_1$–$C_2$)alkyl group, a cinnamyl group, a cyano($C_1$–$C_3$)alkyl group, a carboxy($C_1$–$C_3$)alkyl group, a $C_1$–$C_5$ alkoxycarbonyl($C_1$–$C_3$)alkyl group, a halo($C_1$–$C_5$)alkoxycarbonyl($C_1$–$C_3$)alkyl group, a $C_1$–$C_2$ alkoxy($C_1$–$C_2$)alkoxycarbonyl($C_1$–$C_3$)alkyl group, a $C_1$–$C_5$ alkoxycarbonyl($C_1$–$C_2$)alkoxycarbonyl($C_1$–$C_3$)alkyl group, a cyclo($C_3$–$C_6$)alkoxycarbonyl($C_1$–$C_3$)alkyl group, a $C_1$–$C_5$ alkylaminocarbonyl($C_1$–$C_3$)alkyl group or a di($C_1$–$C_5$)alkylaminocarbonyl($C_1$–$C_3$)alkyl group, which is useful as a herbicide.

10 Claims, No Drawings

BENZOTHIAZOLONES, AND THEIR PRODUCTION AND USE AS HERBICIDES

The present invention relates to benzothiazolones, and their production and use. More particularly, the present invention relates to novel benzothiazolones, a process for producing them, and their use as herbicides.

Some benzothiazolone derivatives (e.g. 4-chloro-2,3-dihydro-2-oxobenzothiazol-3-ylacetic acid (benazolin)) are known to be effective as herbicides [Herbicide Handbook of the Weed Science Society of America, 5th Ed., p. 40 (1983)]. However, their herbicidal activity is not necessarily satisfactory.

It has now been found that the benzothiazolones of the formula:

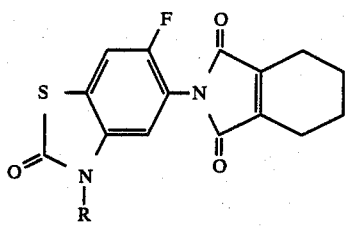

(I)

wherein R is a hydrogen atom, a $C_1$–$C_5$ alkyl group, a $C_3$–$C_4$ alkenyl group, a $C_3$–$C_4$ alkynyl group, a halo($C_1$–$C_4$)alkyl group, a halo($C_3$–$C_4$)alkenyl group, a halo($C_3$–$C_4$)alkynyl group, a $C_1$–$C_2$ alkoxy($C_1$–$C_2$)alkyl group, a $C_1$–$C_2$ alkoxy($C_1$–$C_2$)alkyl group, a cinnamyl group, a cyano($C_1$–$C_3$)alkyl group, a carboxy($C_1$–$C_3$)alkyl group, a $C_1$–$C_5$ alkoxycarbonyl($C_1$–$C_3$)alkyl group, a halo($C_1$–$C_5$)alkoxycarbonyl($C_1$–$C_3$)alkyl group, a $C_1$–$C_2$ alkoxy($C_1$–$C_2$)alkoxycarbonyl($C_1$–$C_3$)alkyl group, a $C_1$–$C_5$ alkoxycarbonyl($C_1$–$C_2$)alkoxycarbonyl($C_1$–$C_3$)alkyl group, a cyclo($C_3$–$C_6$)alkoxycarbonyl($C_1$–$C_3$)alkyl group, a $C_1$–$C_5$ alkylaminocarbonyl($C_1$–$C_3$)alkyl group or a di($C_1$–$C_5$)alkylaminocarbonyl($C_1$–$C_3$)alkyl group exhibit a high herbicidal activity against a wide variety of weeds including broad-leaved weeds, Graminaceous weeds, Commelinaceous weeds and Cyperaceous weeds in agricultural plowed fields by foliar or soil treatments without producing any material phytotoxicity on various agricultural crops such as corn, sorghum, wheat, barley, soybean, peanut and cotton. Examples of the broad-leaved weeds include wild buckwheat (Polygonum convolvulus), ladysthumb (Polygonum pessicaria), pale smartweed (Polygonum lapathifolium), common purslane (Portulaca oleracea), common chickweed (Stellaria media), common lambsquarters (Chenopodium album), redroot pigweed (Amaranthus retroflexus), radish (Raphanus sativus), wild mustard (Sinapis arvensis), shepherdspurse (Capsella bursa-pastoris), hemp sesbania (Sesbania exaltata), sicklepod (Cassia obtusifolia), velvetleaf (Abutilon theophrasti), prickly sida (Sida spinosa), field pansy (Viola arvensis), catchweed bedstraw (Galium aparine), ivyleaf morningglory (Ipomoea hederacea), tall morningglory (Ipomoea purpurea), field bindweed (Convolvulus arvensis), jimsonweed (Datura stramonium), black nightshade (Solanum nigrum), persian speedwell (Veronica persica), common cocklebur (Xanthium pensylvanicum), common sunflower (Helianthus annuus), scentless chamomile (Matricaria perforata), corn marigold (Chrysanthemum segetum), sun spurge (Euphorbia helioscopia), etc. Examples of Graminaceous weeds include Japanese millet (Echinochloa frumentacea), barnyardgrass (Echinochloa crus-galli), sicklepod (Cassia obtusifolia), large crabgrass (Digitaria sanguinalls), annual bluegrass (Poa annua), blackgrass (Alopecurus myosuroides), oats (Avena sativa), wild oats (Avena fatua), johnsongrass (Sorghum halepense), quackgrass (Agropyron repens), downy brome (Bromus tectorum), bermudagrass (Cynodon dactylon), fall panicum (Panicum dichotomiflorum), etc. Examples of Commelinaceous weeds include asiatic dayflower (Commelina communis), etc. Examples of the Cyperaceous weeds include rice flatsedge (cyperus iria), etc.

Particularly, it is notable that the benzothiazolones (I) exhibit a prominent herbicidal activity by soil application before germination of undesired weeds with no material chemical injury. For instance, they show a high herbicidal potency on the broad-leaved weeds such as velvet-leaf, common cocklebur, tall morningglory, sicklepod, prickly sida, jimsonweed, hemp sesbania, reedroot pigweed, common lambsquarters, black nightshade in the field of corn but demonstrate no material phytotoxicity to corn. In the field of sorghum, they exhibit an excellent herbicidal activity on the broad-leaved weeds such as redroot pigweed, velvetleaf, ivyleaf morningglory, tall morningglory and common cocklebur as well as Graminaceous weeds such as johnsongrass, yet they do not demonstrate chemical injury to sorghum. Undesired broad-leaved weeds such as catchweed bedstraw, common chickweed, field pansy, persion speedwell, scentless chamomile, pale smartweed, wild mustard, common lambsquarters, black nightshade and field bindweed and redroot pigweed in the field of wheat or barley can likewise be sufficiently controlled without exerting any material phytotoxicity to wheat or barley. Problematic broad-leaved weeds in the fields of soybeans or peanuts such as velvetleaf, common cocklebur, tall morningglory, sicklepod, prickly sida, jimsonweed, hemp sesbania, redroot pigweed, common lambsquarters and black nightshade can also be controlled with no material phytotoxicity to the soybeans or peanuts. Further, they are highly effective in controlling the broad-leaved weeds such as redroot pigweed, prickly sida, ivyleaf morningglory, tall morningglory, black nightshade and common cocklebur in a field of cotton without causing any material chemical injury to the cotton.

The benzothiazolones (I) of the present invention are also effective in exterminating the paddy field weeds including Graminaceous weeds such as barnyardgrass (Echinochloa oryzicola), broad-leaved weed such as common falsepimpernel (Lindernia procumbens), indian toothcup (Rotala indica) and waterwort (Elatine triandra), Cyperaceous weeds such as Sm.fl. umbrella sedge (Cyperus difformis), hardstem bulrush (Scirpur juncoides) and needle spikerush (Eleocharis acicularis) and others such as monochoria (Monochoria vaginalis) and arrowhead (Sagittaria pygmaea) without producing any phytotoxicity to rice plants on flooding treatment.

Among the benzothiazolones (I), preferred are those wherein R is $C_1$–$C_5$ alkyl, $C_3$–$C_4$ alkenyl, $C_3$–$C_4$ alkynyl, halo($C_1$–$C_4$)alkyl, halo($C_3$–$C_4$)alkyl, halo($C_3$–$C_4$)alkynyl, $C_1$–$C_2$ alkoxy($C_1$–$C_2$)alkyl, $C_1$–$C_2$ alkoxy($C_1$–$C_2$)alkoxy($C_1$–$C_2$)alkyl, etc. More preperred are those wherein R is $C_2$–$C_4$ alkyl, $C_3$–$C_4$ alkenyl, $C_3$–$C_4$ alkynyl group, halopropynyl, etc. The most preferred are those wherein R is $C_2$–$C_3$ alkyl, $C_3$–$C_4$ alkenyl, $C_3$–$C_4$ alkynyl, etc. Typical examples of the preferred compounds are 2-[6-fluoro-3-(1-methylethyl)-2(3H)-benzothiazolon-5-yl]-4,5,6,7-tetrahydro-2H-isoindole- 1,3-dione, 2-[6-fluoro-3-(2-propenyl)-2(3H)benzothaizolon-5-yl]-4,5,6,7-tetrahydro-2H-isoindole-1,3-dione, 2-[6-fluoro-3-(2-propynyl)-2(3H)-benzothiazolon-5-yl]-4,5,6,7-tetrahydro-2H-isoindole-1,3-dione, etc.

The benzothiazolones (I) of the present invention are prepared by reacting an amino compound of the formula:

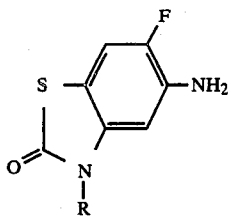

(II)

wherein R is as defined above with 3,4,5,6-tetrahydrophthalic anhydride, usually in a solvent at a temperature of 80° to 200° C. for a period of 1 to 24 hours.

The 3,4,5,6-tetrahydrophthalic anhydride may be used in an amount of about 1 to 3 equivalents to the amino compound (II). Examples of the solvent are aliphatic hydrocarbons (e.g. hexane, heptane, ligroin), aromatic hydrocarbons (e.g. benzene, toluene, xylene), ethers (e.g. diisopropyl ether, dioxane, ethylene glycol dimethyl ether), fatty acids (e.g. formic acid, acetic acid, propionic acid), water, etc. Their mixtures are also usable.

After completion of the reaction, the reaction mixture is subjected to an ordinary post-treatment such as addition of water and collection of precipitated crystals by filtration. Also, it may be subjected to extraction with an organic solvent and concentration. If desired, any conventional purification procedure such as chromatography or recrystallization may be adopted.

Typical examples of the benzothiazolones (I) which may be produced through the above procedure are shown in Table 1.

TABLE 1

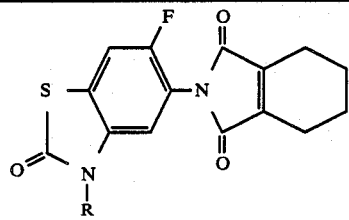

(I)

| R |
|---|
| H |
| CH$_3$ |
| C$_2$H$_5$ |
| n-C$_3$H$_7$ |
| i-C$_3$H$_7$ |
| n-C$_4$H$_9$ |
| i-C$_4$H$_9$ |
| sec-C$_4$H$_9$ |
| t-C$_4$H$_9$ |
| n-C$_5$H$_{11}$ |
| i-C$_5$H$_{11}$ |
| 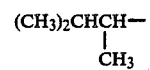 |
| 2-C$_5$H$_{11}$ |
| 3-C$_5$H$_{11}$ |

TABLE 1-continued

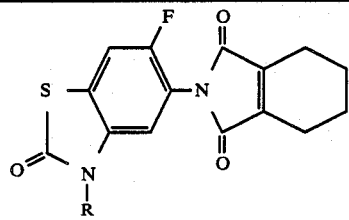

(I)

| R |
|---|
| 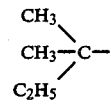 |
| neo-C$_5$H$_{11}$ |
| 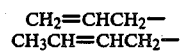 |
| CH$_2$=CHCH$_2$— |
| CH$_3$CH=CHCH$_2$— |
| 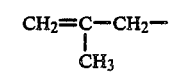 |
| C$_6$H$_5$CH=CHCH$_2$— |
| CH≡CCH$_2$— |
| CH$_3$C≡CCH$_2$— |
|  |
| FCH$_2$— |
| ClCH$_2$— |
| BrCH$_2$— |
| F$_2$CH— |
| Cl$_2$CH— |
| Br$_2$CH— |
| CF$_3$— |
| CCl$_3$— |
| CBr$_3$— |
| FCH$_2$CH$_2$— |
| ClCH$_2$CH$_2$— |
| BrCH$_2$CH$_2$— |
| CF$_3$CF$_3$— |
| 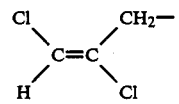 |
| 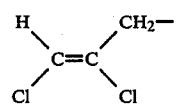 |
| 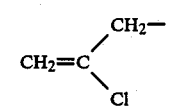 |
| ClCH$_2$CH=CHCH$_2$— |
| CH$_3$(Cl)C=CHCH$_2$— |
| ClCH=CHCH$_2$— |
| 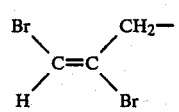 |

TABLE 1-continued

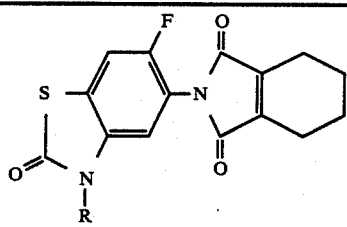

(I)

| R |
|---|
| $\begin{array}{c} H \quad CH_2- \\ C=C \\ Br \quad Br \end{array}$ |
| $\begin{array}{c} CH_2- \\ CH_2=C \\ Br \end{array}$ |
| $BrCH_2CH=CHCH_2-$ |
| $CH_3(Br)C=CHCH_2-$ |
| $BrCH=CHCH_2-$ |
| $ClC\equiv CCH_2-$ |
| $BrC\equiv CCH_2-$ |
| $IC\equiv CCH_2-$ |
| $\begin{array}{c} ClC\equiv C-CH- \\ | \\ CH_3 \end{array}$ |
| $\begin{array}{c} BrC\equiv C-CH- \\ | \\ CH_3 \end{array}$ |
| $\begin{array}{c} IC\equiv C-CH- \\ | \\ CH_3 \end{array}$ |
| $CH_3OCH_2-$ |
| $C_2H_5OCH_2-$ |
| $CH_3OCH_2CH_2-$ |
| $C_2H_5OCH_2CH_2-$ |
| $CH_3OCH_2OCH_2-$ |
| $CH_3OCH_2CH_2OCH_2-$ |
| $C_2H_5OCH_2OCH_2-$ |
| $CH_3OCH_2OCH_2CH_2-$ |
| $C_2H_5OCH_2OCH_2CH_2-$ |
| $C_2H_5OCH_2CH_2OCH_2-$ |
| $C_2H_5OCH_2CH_2OCH_2CH_2-$ |
| $NCCH_2-$ |
| $NCCH_2CH_2-$ |
| $\begin{array}{c} NC-CH- \\ | \\ CH_3 \end{array}$ |
| $\begin{array}{c} HO-C-CH_2- \\ \| \\ O \end{array}$ |
| $\begin{array}{c} HO-C-CH_2CH_2- \\ \| \\ O \end{array}$ |
| $\begin{array}{c} HO-C-CH- \\ \| \quad | \\ O \quad CH_3 \end{array}$ |
| $\begin{array}{c} HO-C-CH- \\ \| \quad | \\ O \quad C_2H_5 \end{array}$ |
| $\begin{array}{c} CH_3O-C-CH_2- \\ \| \\ O \end{array}$ |

TABLE 1-continued

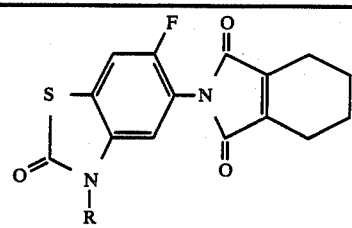

(I)

| R |
|---|
| $\begin{array}{c} C_2H_5O-C-CH_2- \\ \| \\ O \end{array}$ |
| $\begin{array}{c} n\text{-}C_3H_7O-C-CH_2- \\ \| \\ O \end{array}$ |
| $\begin{array}{c} i\text{-}C_3H_7O-C-CH_2- \\ \| \\ O \end{array}$ |
| $\begin{array}{c} n\text{-}C_4H_9O-C-CH_2- \\ \| \\ O \end{array}$ |
| $\begin{array}{c} i\text{-}C_4H_9O-C-CH_2- \\ \| \\ O \end{array}$ |
| $\begin{array}{c} sec\text{-}C_4H_9O-C-CH_2- \\ \| \\ O \end{array}$ |
| $\begin{array}{c} t\text{-}C_4H_9O-C-CH_2- \\ \| \\ O \end{array}$ |
| $\begin{array}{c} n\text{-}C_5H_{11}O-C-CH_2- \\ \| \\ O \end{array}$ |
| $\begin{array}{c} i\text{-}C_5H_{11}O-C-CH_2- \\ \| \\ O \end{array}$ |
| $\begin{array}{c} 3\text{-}C_5H_{11}O-C-CH_2- \\ \| \\ O \end{array}$ |
| $\begin{array}{c} CH_3O-C-CH- \\ \| \quad | \\ O \quad CH_3 \end{array}$ |
| $\begin{array}{c} C_2H_5O-C-CH- \\ \| \quad | \\ O \quad CH_3 \end{array}$ |
| $\begin{array}{c} n\text{-}C_3H_7O-C-CH- \\ \| \quad | \\ O \quad CH_3 \end{array}$ |
| $\begin{array}{c} i\text{-}C_3H_7O-C-CH- \\ \| \quad | \\ O \quad CH_3 \end{array}$ |
| $\begin{array}{c} n\text{-}C_4H_9O-C-CH- \\ \| \quad | \\ O \quad CH_3 \end{array}$ |
| $\begin{array}{c} i\text{-}C_4H_9O-C-CH- \\ \| \quad | \\ O \quad CH_3 \end{array}$ |
| $\begin{array}{c} sec\text{-}C_4H_9O-C-CH- \\ \| \quad | \\ O \quad CH_3 \end{array}$ |

TABLE 1-continued

Structure (I): thiocarbamate with fluoro-phenyl linked to tetrahydrophthalimide; variable R on amide nitrogen.

| R |
|---|
| t-C$_4$H$_9$O—C(=O)—CH(CH$_3$)— |
| n-C$_5$H$_{11}$O—C(=O)—CH(CH$_3$)— |
| i-C$_5$H$_{11}$O—C(=O)—CH(CH$_3$)— |
| 3-C$_5$H$_{11}$O—C(=O)—CH(CH$_3$)— |
| CH$_3$O—C(=O)—CH$_2$CH$_2$— |
| C$_2$H$_5$O—C(=O)—CH$_2$CH$_2$— |
| n-C$_3$H$_7$O—C(=O)—CH$_2$CH$_2$— |
| i-C$_3$H$_7$O—C(=O)—CH$_2$CH$_2$— |
| n-C$_4$H$_9$O—C(=O)—CH$_2$CH$_2$— |
| i-C$_4$H$_9$O—C(=O)—CH$_2$CH$_2$— |
| n-C$_5$H$_{11}$O—C(=O)—CH$_2$CH$_2$— |
| i-C$_5$H$_{11}$O—C(=O)—CH$_2$CH$_2$— |
| FCH$_2$O—C(=O)—CH$_2$— |
| ClCH$_2$O—C(=O)—CH$_2$— |
| BrCH$_2$O—C(=O)—CH$_2$— |
| FCH$_2$CH$_2$O—C(=O)—CH$_2$— |
| ClCH$_2$CH$_2$O—C(=O)—CH$_2$— |
| BrCH$_2$CH$_2$O—C(=O)—CH$_2$— |
| FCH$_2$O—C(=O)—CH(CH$_3$)— |
| ClCH$_2$O—C(=O)—CH(CH$_3$)— |
| BrCH$_2$O—C(=O)—CH(CH$_3$)— |
| FCH$_2$CH$_2$O—C(=O)—CH(CH$_3$)— |
| ClCH$_2$CH$_2$O—C(=O)—CH(CH$_3$)— |
| BrCH$_2$CH$_2$O—C(=O)—CH(CH$_3$)— |
| CH$_3$OCH$_2$O—C(=O)—CH$_2$— |
| C$_2$H$_5$OCH$_2$O—C(=O)—CH$_2$— |
| CH$_3$OCH$_2$CH$_2$O—C(=O)—CH$_2$— |
| C$_2$H$_5$OCH$_2$CH$_2$O—C(=O)—CH$_2$— |
| CH$_3$OCH$_2$O—C(=O)—CH(CH$_3$)— |
| C$_2$H$_5$OCH$_2$O—C(=O)—CH(CH$_3$)— |
| CH$_3$OCH$_2$CH$_2$O—C(=O)—CH(CH$_3$)— |
| C$_2$H$_5$OCH$_2$CH$_2$O—C(=O)—CH(CH$_3$)— |
| CH$_3$O—C(=O)—CH$_2$O—C(=O)—CH$_2$— |

TABLE 1-continued

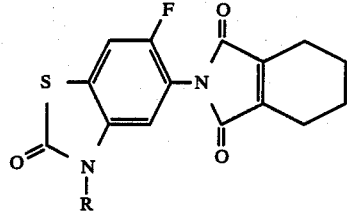

(I)

| R |
|---|
| C₂H₅O—C(=O)—CH₂O—C(=O)—CH₂— |
| CH₃O—C(=O)—CH(CH₃)O—C(=O)—CH₂— |
| CH₃O—C(=O)—CH₂O—C(=O)—CH(CH₃)— |
| C₂H₅O—C(=O)—CH(CH₃)O—C(=O)—CH₂— |
| C₂H₅O—C(=O)—CH₂O—C(=O)—CH(CH₃)— |
| C₂H₅O—C(=O)—CH(CH₃)O—C(=O)—CH(CH₃)— |
| cyclopentyl—O—C(=O)—CH₂— |
| cyclopentyl—O—C(=O)—CH₂CH₂— |
| cyclohexyl—O—C(=O)—CH₂— |
| cyclohexyl—O—C(=O)—CH₂CH₂— |
| cyclopentyl—O—C(=O)—CH(CH₃)— |
| cyclohexyl—O—C(=O)—CH(CH₃)— |
| CH₃NH—C(=O)—CH₂— |
| C₂H₅NH—C(=O)—CH₂— |

TABLE 1-continued

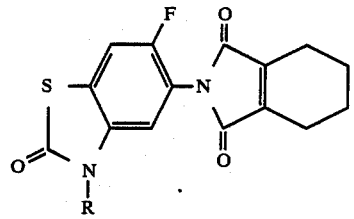

(I)

| R |
|---|
| n-C₃H₇NH—C(=O)—CH₂— |
| i-C₃H₇NH—C(=O)—CH₂— |
| n-C₄H₉NH—C(=O)—CH₂— |
| i-C₄H₉NH—C(=O)—CH₂— |
| n-C₅H₁₁NH—C(=O)—CH₂— |
| i-C₅H₁₁NH—C(=O)—CH₂— |
| n-C₃H₇NH—C(=O)—CH(CH₃)— |
| i-C₃H₇NH—C(=O)—CH(CH₃)— |
| n-C₄H₉NH—C(=O)—CH(CH₃)— |
| i-C₄H₉NH—C(=O)—CH(CH₃)— |
| n-C₃H₇NH—C(=O)—CH(C₂H₅)— |
| i-C₃H₇NH—C(=O)—CH(C₂H₅)— |
| n-C₄H₉NH—C(=O)—CH(C₂H₅)— |
| i-C₄H₉NH—C(=O)—CH(C₂H₅)— |
| (CH₃)₂N—C(=O)—CH₂— |
| CH₃(C₂H₅)N—C(=O)—CH₂— |

TABLE 1-continued (I)

Structure: fluorophenyl with S-C(=O)-N(R)- substituent and tetrahydroisoindole-1,3-dione (attached via N to phenyl)

| R |
|---|
| CH₃\N—C—CH₂— with n-C₃H₇ and O (i.e., N(CH₃)(n-C₃H₇)—C(=O)—CH₂—) |
| CH₃\N—C—CH₂— with n-C₄H₉ and O |
| CH₃\N—C—CH₂— with n-C₅H₁₁ and O |
| C₂H₅\N—C—CH₂— with C₂H₅ and O |
| (CH₃)₂N—C(=O)—CH(CH₃)— |
| CH₃\N—C—CH(CH₃)— with C₂H₅ and O |
| CH₃\N—C—CH(CH₃)— with n-C₃H₇ and O |
| CH₃\N—C—CH(CH₃)— with n-C₄H₉ and O |
| CH₃\N—C—CH(CH₃)— with n-C₅H₁₁ and O |
| (C₂H₅)₂N—C(=O)—CH(CH₃)— |

Practical and presently preferred embodiments for production of the benzothiazolones (I) are illustratively shown in the following Examples.

EXAMPLE 1

5-Amino-6-fluoro-3-(2-propynyl)-2(3H)-benzothiazolone (0.43 g) and 3,4,5,6-tetrahydrophthalic anhydride (0.32 g) were suspended in acetic acid (5 ml), and the resultant suspension was heated under reflux for 5 hours. After being allowed to cool, water was added thereto, and the resultant mixture was extracted with ethyl acetate. The extract was washed with water and an aqueous sodium bicarbonate solution, dried and concentrated. The residue was purified by silica gel thin layer chromatography with a mixture of ethyl acetate and hexane (1:4) to give 2-[6-fluoro-3-(2-propynyl)-2(3H)-benzothiazolon-5-yl]-4,5,6,7-tetrahydro-2H-isoindole-1,3-dione (0.13 g). m.p., 193°–195° C. Recrystallization from 2-propanol gave the purified product. m.p., 198°–199° C.

IR (KBr, CHCl₃) cm⁻¹: 3300, 3020, 1720, 1685, 1490, 1385, 1215, 760, 665.

¹HNMR (CDCl₃, δ): 1.5–2.0 (4H, br.), 2.1–2.6 (5H, br.), 4.61 (2H, d, J=2.6 Hz), 7.06 (1H, d, J=6.0 Hz), 7.27 (1H, d, J=9.0 Hz).

EXAMPLE 2

5-Amino-3-ethoxycarbonylmethyl-6-fluoro-2(3H)benzothiazolone (140 mg) and 3,4,5,6-tetrahydrophthalic anhydride (90 mg) were suspended in acetic acid (3 ml), and the resultant suspension was heated under reflux for 5 hours. After being allowed to cool, water was added thereto, and the resultant mixture was extracted with ethyl acetate. The extract was washed with water and sodium bicarbonate solution, dried and concentrated. The residue was purified by silica gel thin layer chromatography with a mixture of ethyl acetate and hexane (1:2) to give 2-[3-ethoxycarbonylmethyl-6-fluoro-2(3H)-benzothiazolon-5-yl]4,5,6,7-tetrahydro-2H-isoindole-1,3-dione (40 mg). m.p., 155.5°–156.5° C.

In the same manner as above, the benzothiazolones (I) as shown in Table 2 were obtained.

TABLE 2

(I)

Structure: fluorophenyl with S-C(=O)-N(R)- and tetrahydroisoindole-1,3-dione

| Compound No. | R | Physical property |
|---|---|---|
| 1 | H | m.p., 247.5° C. |
| 2 | CH₃ | m.p., 189.5–190.5° C. |
| 3 | C₂H₅ | m.p., 117–119° C. |
| 4 | n-C₃H₇ | m.p., 158–159° C. |
| 5 | i-C₃H₇ | $n_D^{24.4}$ 1.5633 |
| 6 | n-C₄H₉ | m.p., 183–184° C. |
| 7 | i-C₄H₉ | m.p., 182.5–184.0° C. |
| 8 | sec-C₄H₉ | m.p., 180.5–181.0° C. |
| 9 | n-C₅H₁₁ | $n_D^{22.0}$ 1.5691 |
| 10 | i-C₅H₁₁ | $n_D^{21.7}$ 1.5640 |
| 11 | 3-C₅H₁₁ | m.p., 168.5–170.0° C. |
| 12 | CH₂=CHCH₂— | m.p., 136.5–138.5° C. |
| 13 | CH₃CH=CHCH₂— | m.p., 152.5–154.0° C. |
| 14 | CH₂=C(CH₃)—CH₂— | m.p., 85–86° C. |
| 15 | C₆H₅CH=CHCH₂— | m.p., 62.5–64.0° C. |
| 16 | CH≡CCH₂— | m.p., 193–195° C. |
| 17 | CH≡C—CH(CH₃)— | m.p., 110–111 |
| 18 | FCH₂CH₂— | $n_D^{25.2}$ 1.5763 |
| 19 | ClCH₂CH₂— | m.p., 180.5° C. |
| 20 | BrCH₂CH₂— | m.p., 195° C. |

TABLE 2-continued

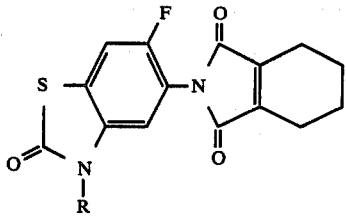

| Compound No. | R | Physical property |
|---|---|---|
| 21 | Cl-CH=C(H)-CH2-Cl (cis) | m.p., 59–60° C. |
| 22 | H-C(Cl)=C(Cl)-CH2- | m.p., 191–192° C. |
| 23 | CH2=C(Cl)-CH2- | m.p., 151–153° C. |
| 24 | ClCH2CH=CHCH2— | $n_D^{21.0}$ 1.5824 |
| 25 | CH3(Cl)C=CHCH2— | $n_D^{18.5}$ 1.5870 |
| 26 | ClCH=CHCH2— | $n_D^{20.0}$ 1.5844 |
| 27 | BrC≡CCH2— | m.p., 192.5–194.0° C. |
| 28 | CH3OCH2— | m.p., 155–156° C. |
| 29 | C2H5OCH2— | m.p., 194–195° C. |
| 30 | CH3OCH2CH2OCH2— | m.p., 123–125° C. |
| 31 | NCCH2— | m.p., 195–196° C. |
| 32 | NCCH2CH2— | m.p., 192° C. |
| 33 | HO—C(O)—CH2— | m.p., 289.4° C. |
| 34 | CH3O—C(O)—CH2— | m.p., 222.0–223.0° C. |
| 35 | C2H5O—C(O)—CH2 | m.p., 155.5–156.5° C. |
| 36 | n-C5H11O—C(O)—CH2— | $n_D^{27.2}$ 1.5520 |
| 37 | CH3O—C(O)—CH(CH3)— | m.p., 164.0–165.0° C. |
| 38 | CH3O—C(O)—CH2CH2— | m.p., 174.9° C. |
| 39 | n-C4H9O—C(O)—CH2CH2— | $n_D^{29.0}$ 1.5616 |
| 40 | ClCH2CH2O—C(O)—CH2— | $n_D^{29.0}$ 1.5800 |
| 41 | CH3OCH2CH2O—C(O)—CH2— | m.p., 200.5–202.0° C. |
| 42 | C2H5O—C(O)—CH(CH3)—O—C(O)—CH2— | $n_D^{29.0}$ 1.5531 |
| 43 | cyclopentyl-O—C(O)—CH2— | $n_D^{27.7}$ 1.5508 |
| 44 | cyclopentyl-O—C(O)—CH2CH2— | m.p., 80–82° C. |
| 45 | cyclohexyl-O—C(O)—CH2CH2— | $n_D^{29.0}$ 1.5752 |
| 46 | (CH3)2CHCH2NH—C(O)—CH(C2H5)— | $n_D^{28.5}$ 1.5383 |
| 47 | (CH3)(n-C4H9)N—C(O)—CH(CH3)— | $n_D^{28.5}$ 1.5464 |

The amino compound (II) as the starting material in the process of this invention may be produced according to the following scheme:

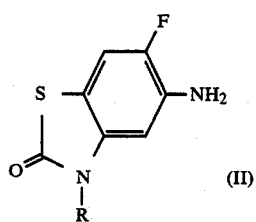

(II)

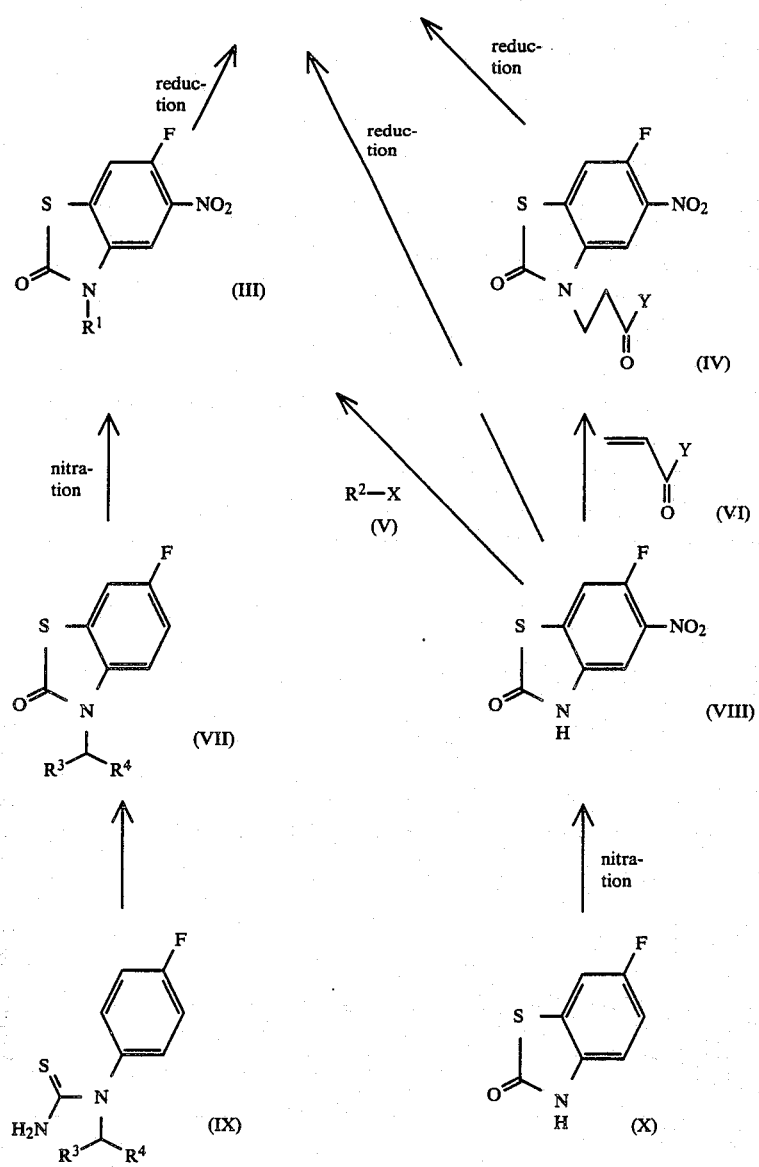

wherein R is as defined above and $R^1$ has the same meaning as R except for carboxyethyl, 2-($C_1$-$C_5$)alkoxycarbonylethyl, 2-halo($C_1$-$C_5$)alkoxycarbonylethyl, 2-($C_1$-$C_2$)alkoxy($C_1$-$C_2$)alkoxycarbonylethyl, 2-($C_1$-$C_5$)alkoxycarbonyl($C_1$-$C_2$)alkoxycarbonylethyl, 2-cyclo($C_3$-$C_6$)alkoxycarbonylethyl, 2-($C_1$-$C_5$)alkylaminocarbonylethyl and 2-di($C_1$-$C_5$)alkylaminocarbonylethyl, $R^2$ has the same meaning as $R^1$ except for $$-\underset{\underset{R^3}{|}}{C}H-R^4,$$

$R^3$ and $R^4$ are each $C_1$-$C_4$ alkyl but the total number of carbon atoms in $R^3$ and $R^4$ does not exceed 4, X is chlorine, bromine, iodine, methanesulfonyloxy or p-toluenesulfonyloxy, and Y is hydroxyl, $C_1$-$C_5$ alkoxy, halo($C_1$-$C_5$)alkoxy, $C_1$-$C_2$ alkoxy($C_1$-$C_2$)alkoxy, $C_1$-$C_5$ alkoxycarbonyl($C_1$-$C_2$)alkoxy, cyclo($C_3$-$C_6$)alkoxy, $C_1$-$C_5$ alkylamino or di($C_1$-$C_5$)alkylamino.

Each reaction as set forth above will be hereinafter explained in detail.

(1) Production of the compound (II) from the compound (III), (IV) or (VIII) (Procedure 1):

The compound (II) is synthesized by reacting the compound (III), (IV) or (VIII) with a reducing agent (e.g. iron powder) at a temperature of 60° to 120° C. for a period of 10 minutes to 12 hours. Preferably, the reaction is effected in a solvent such as acetic acid and ethyl acetate. In the reaction, the reducing agent is used in an amount of 3 to 30 equivalents, preferably of 5 to 20 equivalents, to one equivalent of the compound (III), (IV) or (VIII).

After completion of the reaction, the residue is collected by filtration, and the filtrate is washed with an organic solvent. The extract is washed with water and a sodium bicarbonate solution and subjected to concentration to obtain the compound (II). If necessary, any purification method such as recrystallization or chromatography may be applied to the product.

(2) Production of the compound (III) from the compound (VIII) (Procedure 2):

The compound (III) is prepared by reacting the compound (VIII) with the compound (V) in the presence of a base (e.g. sodium hydride, potassium carbonate, sodium hydroxide, potassium hydroxide), at a temperature of 0° to 120° C. for a period of 30 minutes to 24 hours in a solvent such as an aromatic hydrocarbon (e.g. toluene, benzene), an amide (e.g. N,N-dimethylformamide), a sulfur compound (e.g. dimethylsulfoxide), a nitrile (e.g. acetonitrile) or water, or their mixture. In the reaction, the compound (V) and the base are respectively used in an amount of 1 to 1.5 equivalents to one equivalent of the compound (VIII). The recovery of the compound (III) can be accomplished by adding water to the reaction mixture, extracting the resultant mixture with an organic solvent and concentrating the extract. When desired, any purification procedure such as recrystallization or chromatography may be adopted.

(3) Production of the compound (IV) from the compound (VIII) (Procedure 3):

The compound (IV) can be obtained by reacting the compound (VIII) with the compound (VI) in the presence of a base (e.g. benzyl trimethylammonium hydroxide) at a temperature of 50° to 100° C. for a period of 30 minutes to 24 hours, ordinarily in a solvent such as an aromatic hydrocarbon (e.g. toluene, benzene), an amide (e.g. N,N-dimethylformamide), a sulfur compound (e.g. dimethylsulfoxide), a nitrile (e.g. acetonitrie) or water, or their mixture. In the reaction, the compound (VI) and the base are respectively used in an amount of 1.0 equivalent to excess and 1.0 to 3 equivalents to one equivalent of the compound (VIII). The recovery of the compound (IV) can be accomplished by adding water to the reaction mixture, extracting the resultant mixture with an organic solvent and concentrating the extract. When desired, any purification procedure such as recrystallization or chromatography may be adopted.

(4) Production of the compound (VIII) (Procedure 4):

The compound (VIII) is obtained by reacting the compound (X) with a nitrating agent (e.g. a mixture of sulfuric acid and nitric acid) at a temperature of $-10°$ to 10° C. instantaneously or within 5 hours. In the reaction, sulfuric acid and nitric acid are used respectively in an amount of 1 equivalent to excess and 1 to 1.2 equivalents to one equivalent of the compound (X). After completion of the reaction, the resultant mixture is subjected to a conventional post-treatment. For instance, it is poured into ice-water, and precipitated crystals are collected by filtration and washed with water. When desired, the resulting product may be further purified by recrystallization or chromatography.

Still, the starting compound (X) may be prepared according to the method as described in G. Mazzone and G. Pappalaro: Farmaco, Ed., Sc., 32 (5), 348 (1977).

(5) Production of the compound (III) (Procedure 5):

The compound (III) may be synthesized by reacting the compound (VII) with a nitrating agent (e.g. a mixture of sulfuric acid and nitric acid) at a temperature of $-10°$ to 10° C. instantaneously or within 5 hours. In the reaction, sulfuric acid and nitric acid are used respectively in an amount of 1 equivalent to amount and 1 to 1.2 equivalents to one equivalent of the compound (VII). After completion of the reaction, the resultant mixture is subjected to a conventional post-treatment. For instance, it is poured into ice-water, and precipitated crystals are collected by filtration and washed with water. When desired, the resulting product may be further purified by recrystallization or chromatography.

(6) Production of the compound (VII):

The compound (VII) can be prepared from the compound (IX) by the method as described in Japanese Patent Publication (unexamined) Nos. 123480/1985 and 166673/1985.

The intermediates, i.e. the compounds (II), (III), (IV) and (VIII), are novel and can be represented by the general formula:

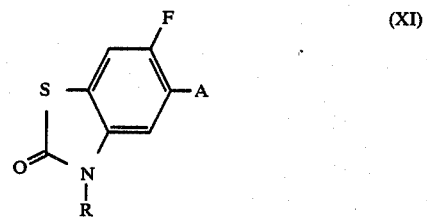

wherein R is as defined above and A is amino or nitro.

Typical examples for production of the intermediates are illustratively shown in the following examples.

EXAMPLE 3

Procedure 1

Electrolytic iron powder (0.77 g) was suspended in 5% acetic acid (1.5 ml), and the suspension was heated to 80° C. A solution of 3-allyl-6-fluoro-5-nitro-2(3H)-benzothiazolone (0.70 g) in acetic acid (2.8 ml) and ethyl acetate (2.8 ml) was added thereto. The resultant mixture was heated under reflux at a temperature of 60° to 80° C. for 3 hours. After being allowed to cool, water and ethyl acetate were added thereto, the precipitate was collected by filtration, and the filtrate was extracted with ethyl acetate. The extract was washed with water and sodium bicarbonate solution, dried and concentrated to give 0.60 g of 5-amino-3-allyl-6-fluoro-2(3H)-benzothiazolone. $n_D^{26.0}$ 1.6236.

EXAMPLE 4

Procedure 1

Electrolytic iron powder (0.29 g) was suspended in 5% acetic acid (2 ml), and a solution of 3-ethoxycarbonylmethyl-6-fluoro-5-nitro-2(3H)-benzothiazolone (0.31 g) in acetic acid (1 ml) and ethyl acetate (1 ml) was dropwise added thereto while heating. The resultant mixture was heated under reflux for 3 hours. The reaction mixture was subjected to filtration with celite, and the filtrate was extracted with ethyl acetate. The extract was washed with water and sodium bicarbonate solution, dried and concentrated to give 0.20 g of 5-amino-3-ethoxycarbonylmethyl-6-fluoro-2(3H)-benzothiazolone. m.p., 172.5°–173.5° C.

In the same manner as above, the compounds (II) as shown in Table 3 were obtained.

TABLE 3 (II)

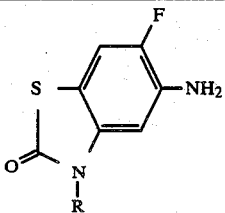

| R | Physical property |
|---|---|
| H | |
| CH₃ | m.p., 188–189° C. |
| C₂H₅ | m.p., 117–119° C. |
| n-C₃H₇ | $n_D^{25.3}$ 1.6000 |
| i-C₃H₇ | $n_D^{24.4}$ 1.6056 |
| n-C₄H₉ | $n_D^{22.0}$ 1.5910 |
| i-C₄H₉ | m.p., 113–114° C. |
| sec-C₄H₉ | $n_D^{23.5}$ 1.5933 |
| n-C₅H₁₁ | $n_D^{22.0}$ 1.5691 |
| i-C₅H₁₁ | $n_D^{21.7}$ 1.5824 |
| 3-C₅H₁₁ | m.p., 102° C. |
| CH₂=CHCH₂— | $n_D^{26.0}$ 1.6236 |
| CH₂=C(CH₃)—CH₂— | m.p., 96–97° C. |
| C₆H₅CH=CHCH₂— | m.p., 104.5–105.0° C. |
| CH≡CCH₂— | m.p., 124–126° C. |
| CH≡C—CH(CH₃)— | m.p., 128.5–129.5° C. |
| FCH₂CH₂— | m.p., 133–134° C. |
| ClCH₂CH₂— | m.p., 126.5–128.0° C. |
| BrCH₂CH₂— | m.p., 113–114° C. |
| (Cl)(H)C=C(Cl)(CH₂—) | m.p., 140–142° C. |
| (H)(Cl)C=C(Cl)(CH₂—) | m.p., 142.5–143.5° C. |
| CH₂=C(Cl)(CH₂—) | m.p., 136–137° C. |
| ClCH₂CH=CHCH₂— | m.p., 237–239° C. |
| (H₃C)(Cl)C=C(H)(CH₂—) | m.p., 103–104° C. |
| (Cl)(H₃C)C=C(H)(CH₂—) | m.p., 90.5–91.0° C. |
| (Cl)(H)C=C(H)(CH₂—) | m.p., 139–140° C. |
| (H)(Cl)C=C(H)(CH₂—) | $n_D^{21.0}$ 1.6323 |

TABLE 3-continued (II)

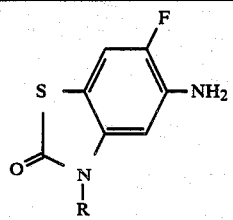

| R | Physical property |
|---|---|
| BrC≡CCH₂— | m.p., 174.5–175.0° C. |
| CH₃OCH₂— | m.p., 112–113° C. |
| C₂H₅OCH₂— | m.p., 77–78° C. |
| CH₃OCH₂CH₂OCH₂— | m.p., 99.5–100.5° C. |
| NCCH₂— | m.p., 153.5–154.5° C. |
| NCCH₂CH₂— | m.p., 175° C. |
| HO—C(O)—CH₂— | resinous |
| CH₃O—C(O)—CH₂— | m.p., 155.5–156.5° C. |
| C₂H₅O—C(O)—CH₂— | m.p., 172.5–173.5° C. |
| n-C₅H₁₁O—C(O)—CH₂— | $n_D^{27.7}$ 1.5651 |
| CH₃O—C(O)—CH(CH₃)— | m.p., 120.0–125.0° C. |
| CH₃O—C(O)—CH₂CH₂— | m.p., 124.1° C. |
| n-C₄H₉O—C(O)—CH₂CH₂— | m.p., 79.1° C. |
| CH₃OCH₂CH₂O—C(O)—CH₂— | m.p., 155–157° C. |
| C₂H₅O—C(O)—CH(CH₃)—C(O)—CH₂— | visous solid |
| cyclopentyl-O—C(O)—CH₂— | $n_D^{27.7}$ 1.5642 |
| cyclopentyl-O—C(O)—CH₂CH₂— | $n_D^{28.0}$ 1.5744 |
| cyclohexyl-O—C(O)—CH₂CH₂— | $n_D^{29.0}$ 1.5655 |
| (CH₃)₂CHCH₂NH—C(O)—CH(C₂H₅)— | resinous |

TABLE 3-continued (II) Structure: benzothiazolone with F and NH₂ substituents, N-R group on the thiazolone nitrogen.

| R | Physical property |
|---|---|
| CH₃\N—C—CH—<br>n-C₄H₉ / ‖ \|<br>O CH₃ | $n_D^{28.5}$ 1.5556 |

EXAMPLE 5

Procedure 2

60% Oily sodium hydride (0.21 g) was suspended in N,N-dimethylformamide (7 ml), and the resultant suspension was cooled to 0° C. 6-Fluoro-5-nitro-2(3H)-benzothiazolone (1.0 g) was added thereto at 0° to 5° C., and the mixture was stirred for 30 minutes. Allyl bromide (0.62 g) was added to the reaction mixture, and the temperature was gradually elevated to a temperature of 50° to 60° C. The mixture was allowed to react at that temperature for 3 hours. Water was added to the mixture, which was extracted with ethyl acetate. The extract was washed with water, dried and concentrated. The residue was purified by silica gel thin layer chromatography with a mixture of ethyl acetate and toluene (1:9) to give 0.70 g of 3-allyl-7-fluoro-6-nitro-2(3H)-benzothiazolone. m.p., 112.5°–113.5° C.

EXAMPLE 6

Procedure 2

50% Oily sodium hydride (0.21 g) was suspended in N,N-dimethylformamide (5 ml), and the resultant suspension was cooled to 0° C. 6-Fluoro-5-nitro-2-(3H)-benzothiazolone (1.0 g) was portionwise added thereto at 0° C., and the mixture was stirred at the same temperature for 30 minutes. Ethyl bromoacetate (0.86 g) was added to the reaction mixture at 0° C., and the temperature was gradually elevated to a temperature of 50° to 60° C., followed by stirring at that temperature for 3 hours. Water was added to the mixture, which was extracted with ethyl acetate. The extract was washed with water, dried and concentrated. The residue was purified by silica gel thin layer chromatography with a mixture of ethyl acetate and toluene (1:9) to give 0.35 g of 3-ethoxycarbonylmethyl-6-fluoro-5-nitro-2(3H)-benzothiazolone. m.p., 139.0°–140.0° C.

EXAMPLE 7

Procedure 3

A mixture of 6-fluoro-5-nitro-2-(3H)-benzothiazolone (1.0 g), methyl acrylate (5 ml) and a 40% methanolic solution of benzyltrimethylammonium hydroxide (1.95 g) was heated under reflux for 2 hours, followed by cooling. Water was added to the reaction mixture, which was extracted with ethyl acetate. The extract was washed with water, dried and concentrated to give 1.12 g of 6-fluoro-3-(2-methoxycarbonyl)ethyl-5-nitro-2(3H)-benzothiazolone. m.p., 224.3° C.

EXAMPLE 8

Procedure 5

6-Fluoro-3-(1-methylethyl)-2-(3H)-benzothiazolone (299 g) was dissolved in concentrated sulfuric acid (8750 g), and the resultant mixture was cooled to a temperature of −5° to 0° C. 98% fuming nitric acid (d=1.52) (94.68 g) was dropwise added thereto while maintaining the temperature at 0° C., followed by stirring for 1 hour. The reaction mixture was poured into ice-water (16 kg), and the precipitated crystals were collected by filtration. Crystals were washed with water and dried to give 325 g of 6-fluoro-3-(1-methylethyl)-5-nitro-2(3H)-benzothiazolone. m.p., 153°–153.5° C.

In the same manner as above, the compounds (III) or (IV) as shown in Table 4 were obtained.

TABLE 4

Structure: benzothiazolone with F and NO₂ substituents, N-R group on the thiazolone nitrogen.

| R | Physical property |
|---|---|
| CH₃ | m.p., 148–149° C. |
| C₂H₅ | m.p., 128–128.5° C. |
| n-C₃H₇ | m.p., 71–73° C. |
| i-C₃H₇ | m.p., 153–153.5° C. |
| n-C₄H₉ | m.p., 83–84° C. |
| i-C₄H₉ | m.p., 101.5–103.0° C. |
| sec-C₄H₉ | m.p., 87–88° C. |
| n-C₅H₁₁ | m.p., 68.5–69.5° C. |
| i-C₅H₁₁ | $n_D^{22.0}$ 1.5900 |
| 3-C₅H₁₁ | m.p., 110–111° C. |
| CH₂=CHCH₂— | m.p., 112.5–113.5° C. |
| CH₃CH=CHCH₂— | m.p., 84–85° C. |
| CH₂=C—CH₂—<br>    \|<br>    CH₃ | m.p., 83–84° C. |
| C₆H₅CH=CHCH₂ | m.p., 106–107° C. |
| CH≡CCH₂— | m.p., 123.5–124.5° C. |
| CH≡C—CH—<br>       \|<br>       CH₃ | m.p., 183.5–184.5° C. |
| FCH₂CH₂— | m.p., 136–137° C. |
| ClCH₂CH₂— | m.p., 125–126° C. |
| BrCH₂CH₂— | m.p., 128.5–129.5° C. |
| Cl\ /CH₂—<br>  C=C<br>H/  \Cl | $n_D^{22.5}$ 1.6224 |
| H\ /CH₂—<br>  C=C<br>Cl/ \Cl | m.p., 133° C. |
| CH₂— \<br>CH₂=C<br>       \Cl | $n_D^{22.2}$ 1.6340 |
| ClCH₂CH=CHCH₂— | $n_D^{21.7}$ 1.6217 |
| CH₃(Cl)C=CHCH₂— | $n_D^{18.5}$ 1.6153 |

TABLE 4-continued

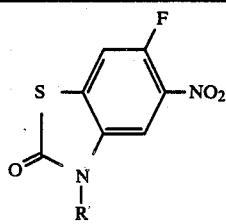

| R | Physical property |
|---|---|
| ClCH=CHCH$_2$— | $n_D^{18.5}$ 1.6287 |
| BrC≡CCH$_2$— | m.p., 134.5–136.0° C. |
| CH$_3$OCH$_2$— | m.p., 125–126° C. |
| C$_2$H$_5$OCH$_2$— | m.p., 114–115° C. |
| CH$_3$OCH$_2$CH$_2$OCH$_2$— | m.p., 78–80° C. |
| NCCH$_2$— | m.p., 146.5–147.5° C. |
| NCCH$_2$CH$_2$— | m.p., 174–176° C. |
| HO—C(=O)—CH$_2$— | m.p., 264.2° C. |
| CH$_3$O—C(=O)—CH$_2$— | m.p., 163.5–165.0° C. |
| C$_2$H$_5$O—C(=O)—CH$_2$— | m.p., 139.0–140.0° C. |
| n-C$_5$H$_{11}$O—C(=O)—CH$_2$— | m.p., 75.0–76.0° C. |
| CH$_3$O—C(=O)—CH(CH$_3$)— | m.p., 124.5–125.5° C. |
| CH$_3$O—C(=O)—CH$_2$CH$_2$— | m.p., 224.3° C. |
| n-C$_4$H$_9$O—C(=O)—CH$_2$CH$_2$— | m.p., 79.1° C. |
| ClCH$_2$CH$_2$O—C(=O)—CH$_2$— | m.p., 118.0–120.0° C. |
| CH$_3$OCH$_2$CH$_2$O—C(=O)—CH$_2$— | m.p., 90.5–91.5° C. |
| C$_2$H$_5$O—C(=O)—CH(CH$_3$)—C(=O)—CH$_2$— | m.p., 110.0–112.0° C. |
| cyclopentyl-O—C(=O)—CH$_2$— | m.p., 121.5–123.0° C. |
| cyclopentyl-O—C(=O)—CH$_2$CH$_2$— | $n_D^{29.0}$ 1.5914 |
| cyclohexyl-O—C(=O)—CH$_2$CH$_2$— | $n_D^{29.0}$ 1.5743 |

TABLE 4-continued

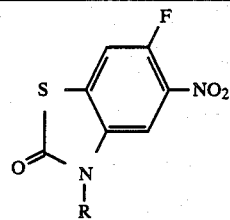

| R | Physical property |
|---|---|
| (CH$_3$)(n-C$_4$H$_9$)N—C(=O)—CH(CH$_3$)— | $n_D^{28.5}$ 1.5445 |

EXAMPLE 9

Procedure 4

6-Fluoro-2(3H)-benzothiazolone (47.58 g) was dissolved in 100% sulfuric acid (760 ml), and the resultant mixture was cooled to 0° to 5° C. 98% fuming nitric acid (d=1.52) (18.79 g) was gradually added thereto at a temperature of 0° to 5° C., followed by stirring at the same temperature for 60 minutes. The reaction mixture was poured into ice-water. The precipitated crystals were collected by filtration, washed with water and air-dried to give 48.48 g of 6-fluoro-5-nitro-2(3H)-benzothiazolone as pale brown crystals. m.p., 180°–182° C.

In the practical use of the benzothiazolones (I), they may be applied in conventional preparation forms such as emulsifiable concentrates, wettable powders, suspensions and granules in combination with conventional solid or liquid carriers of diluents as well as surface active agents or auxiliary agents. The content of the benzothiazolones (I) as the active ingredient in such preparation forms is usually within a range of 0.05 to 90% by weight, preferably of 0.1 to 80% by weight. Examples of the solid carrier or diluent are fine powders or granules of kaolin clay, attapulgite clay, bentonite, terra alba, pyrophyllite, talc, diatomaceous earth, calcite, walnut powders, urea, ammonium sulfate and synthetic hydrous silicate, etc. As the liquid carrier or diluent, there may be exemplified aromatic hydrocarbons (e.g. xylene, methylnaphthalene), alcohols (e.g. isopropanol, ethylene glycol, cellosolve), ketones (e.g. acetone, cyclohexanone, isophorone), soybean oil, cotton seed oil, dimethylsulfoxide, N,N-dimethylformamide, acetonitrile, water, etc.

The surface active agent used for emulsification, dispersion or spreading may be any of the anionic and non-ionic type of agents. Examples of the surface active agent include alkylsulfates, alkylarylsulfonates, dialkylsulfosuccinates, phosphates of polyoxyethylenealkylaryl ethers, polyoxyethylene alkyl ethers, polyoxyethylene alkylaryl ethers, polyoxyethylene polyoxypropylene block copolymer, sorbitan fatty acid esters, polyoxyethylene sorbitan fatty acid esters, etc. Examples of the auxiliary agents include ligninsulfonates, sodium alginate, polyvinyl alcohol, gum arabic, CMC (carboxymethyl cellulose), PAP (isopropyl acid phosphate), etc.

Practical embodiments of the herbicidal composition according to the invention are illustratively shown in the following examples wherein parts are by weight.

The compound number of the active ingredient corresponds to the one in Table 1.

Formulation Example 1

Fifty parts of Compound No. 2, 4, 34 or 35, 3 parts of calcium ligninsulfonate, 2 parts of sodium laurylsulfate and 45 parts of synthetic hydrous silicate are well mixed while being powdered to obtain a wettable powder.

Formulation Example 2

Five parts of Compound No. 5, 14 parts of polyoxyethylenestyrylphenyl ether, 6 parts of calcium dodecylbenzenesulfonate, 30 parts of xylene and 45 parts of cyclohexanone are well mixed to obtain an emulsifiable concentrate.

Formulation Example 3

Ten parts of Compound No. 37 or 43, 14 parts of polyoxyethylenestyrylphenyl ether, 6 parts of calcium dodecylbenzenesulfonate, 25 parts of xylene and 45 parts of cyclohexanone are well mixed to obtain an emulsifiable concentrate.

Formulation Example 4

Two parts of Compound No. 3, 12, 16, 34 or 44, 1 part of synthetic hydrous silicate, 2 parts of calcium ligninsulfonate, 30 parts of bentonite and 65 parts of kaolin clay are well mixed while being powdered. The mixture is then kneaded with water, granulated and dried to obtain granules.

Formulation Example 5

Twenty-five parts of Compound No. 4, 16, 29, 37 or 41 is mixed with 3 parts of polyoxyethylene sorbitan monooleate, 3 parts of carboxymethyl cellulose and 69 parts of water and pulverized until the particle size of the mixture becomes less than 5 microns to obtain a suspension.

Formulation Example 6

Five parts of Compound No. 2, 3,4, 5, 12, 16, 17, 28, 29, 31, 36 or 38, 14 parts of polyoxyethylenestyrylphenyl ether, 6 parts of calcium dodecylbenzenesulfonate, 30 parts of xylene and 45 parts of N,N-dimethylformamide are well mixed to obtain an emulsifiable concentrate.

The benzothiazolones (I) thus formulated in any suitable formulation form are useful for the pre-emergence or post-emergence control of undesired weeds by soil or foliar treatment as well as flood fallowing treatment. These treatments include the application to the soil surface prior to or after the transplanting or the incorporation into the soil. The foliar treatment may be effected by spraying the herbicidal composition containing the benzothiazolones (I) over the top of the plants. It may also be applied directly to the weeds if care is taken to keep the chemical off the crop foliage.

The benzothiazolones (I) of the present invention may be used together with other herbicides to improve their activity as herbicides, and in some cases, a synergistic effect can be expected. Further, they may be applied in combination with insecticides, acaricides, nematocides, fungicides, plant growth regulators, fertilizers, soil improvers, etc.

Furthermore, the benzothiazolones (I) can be used as herbicides applicable to agricultural plowed fields as well as paddy fields. They are also useful as herbicides to be employed for orchards, pasture lands, lawns, forests, non-agricultural fields, etc.

The dosage rate of the benzothiazolones (I) may vary depending on prevailing weather conditions, the formulation used, the prevailing season, the mode of application, the soil involved, the crop and weed species, etc. Generally, however, the dosage rate is from 0.02 to 100 grams, preferably from 0.05 to 50 grams, of the active ingredient per are. The herbicidal composition of the invention formulated in the form of an emulsifiable concentrate, a wettable powder or a suspension may ordinarily be employed by diluting it with water at a volume of 1 to 10 liters per are, if necessary, with addition of an auxiliary agent such as a spreading agent. Examples of the spreading agent include, in addition to the surface active agents as noted above, polyoxyethylene resin acid (ester), ligninsulfonate, abiethylenic acid salt, dinaphthylmethanedisulfonate, paraffin, etc. The composition formulated in the form of granules may be normally applied as such without dilution.

The biological data of the benzothiazolones (I) as herbicides will be illustratively shown in the following Examples wherein the phytotoxicity to crop plants and the herbicidal activity on weeds were observed visually as to the degree of germination as well as the growth inhibition and rated with an index 0, 1, 2, 3, 4 or 5, in which the numeral "0" indicates no material difference as seen in comparison with the untreated plant and the numeral "5" indicates the complete inhibition or death of the test plants.

The compounds shown in Table 5 below were used for comparison.

TABLE 5

| Compound No. | Chemical structure | Remarks |
| --- | --- | --- |
| A | Cl, CH$_2$COOH, N, =O, S (benzothiazole structure) | Commercially available herbicide "benazolin" |
| B | Cl, triazine with H$_3$C\\N≡C—C—N—C, /H, N, C—N—C$_2$H$_5$, H$_3$C / H | Commercially available herbicide "cyanazin" |

Test Example 1

Cylindrical plastic pots (diameter, 10 cm; height, 10 cm) were filled with upland field soil, and the seeds of Japanese millet, oats, tall morningglory and velvetleaf were sowed therein and covered with soil. A designated amount of the test compound formulated in an emulsifiable concentrate according to Formulation Example 2, 3 or 6 was diluted with water, and the dilution was sprayed onto the soil surface by means of a small hand sprayer at a spray volume of 10 liters per are. The test plants were further grown in a greenhouse for 20 days, and the herbicidal activity was examined. The results are shown in Table 6.

TABLE 6

| | | Herbicidal activity | | | |
| --- | --- | --- | --- | --- | --- |
| Compound No. | Dosage (g/are) | Japanese millet | Oats | Tall morningglory | Velvetleaf |
| 2 | 20 | 5 | 5 | 5 | 5 |
| 3 | 20 | 5 | 5 | 5 | 5 |
| 4 | 20 | 5 | 5 | 5 | 5 |
| 5 | 20 | 5 | 5 | 5 | 5 |
| 6 | 20 | 5 | 5 | 5 | 5 |
| 7 | 20 | 4 | — | 5 | 5 |
| 8 | 20 | 5 | 5 | 5 | 5 |
| 9 | 20 | 4 | 4 | 5 | 5 |
| 10 | 20 | 4 | 4 | 4 | 5 |

TABLE 6-continued

| Compound No. | Dosage (g/are) | Herbicidal activity | | | |
|---|---|---|---|---|---|
| | | Japanese millet | Oats | Tall morningglory | Velvetleaf |
| 12 | 20 | 5 | 5 | 5 | 5 |
| 13 | 20 | 4 | 4 | 4 | 5 |
| 14 | 20 | 4 | 4 | 5 | 5 |
| 16 | 20 | 5 | 5 | 5 | 5 |
| 17 | 20 | 5 | 5 | 5 | 5 |
| 18 | 20 | 5 | 5 | 5 | 5 |
| 19 | 20 | 5 | 5 | 5 | 5 |
| 20 | 20 | 5 | 4 | 4 | 5 |
| 22 | 20 | 5 | — | 4 | 5 |
| 25 | 20 | — | — | 5 | 5 |
| 26 | 20 | 5 | 4 | 5 | 5 |
| 27 | 20 | 5 | 5 | 5 | 5 |
| 28 | 20 | 5 | 5 | 5 | 5 |
| 29 | 20 | 5 | 5 | 5 | 5 |
| 30 | 20 | 5 | 5 | 5 | 5 |
| 31 | 20 | 5 | 5 | 5 | 5 |
| 32 | 20 | 5 | 5 | 5 | 5 |
| 35 | 20 | — | — | 5 | 5 |
| 37 | 20 | 5 | — | 5 | 5 |
| 38 | 20 | — | — | 4 | 5 |
| 39 | 20 | — | — | 5 | 5 |
| 41 | 20 | — | — | 5 | 5 |
| 44 | 20 | — | — | 5 | 5 |
| 45 | 20 | — | — | 5 | 5 |
| 47 | 20 | 5 | — | 5 | 5 |

Test Example 2

Cylindrical plastic pots (diameter, 10 cm; height, 10 cm) were filled with upland field soil, and the seeds of Japanese millet, radish and velvetleaf were sowed therein and cultivated in a greenhouse for 10 days. A designated amount of the test compound formulated in an emulsifiable concentrate according to Formulation Example 2, 3 or 6 was diluted with water containing a spreading agent, and the dilution was sprayed over the foliage of the test plants by means of a small hand sprayer at a spray volume of 10 liters per are. The test plants were further grown in the greenhouse for 20 days, and the herbicidal activity was examined. The results are shown in Table 7.

TABLE 7

| Compound No. | Dosage (g/are) | Herbicidal activity | | |
|---|---|---|---|---|
| | | Japanese millet | Radish | Velvetleaf |
| 1 | 20 | 5 | 5 | 5 |
| 2 | 20 | 5 | 5 | 5 |
| 3 | 20 | 5 | 5 | 5 |
| 4 | 20 | 5 | 5 | 5 |
| 5 | 20 | 4 | 5 | 5 |
| 6 | 20 | 5 | 5 | 5 |
| 7 | 20 | 5 | 5 | 5 |
| 8 | 20 | 5 | 5 | 5 |
| 9 | 20 | 5 | 5 | 5 |
| 10 | 20 | 5 | 5 | 5 |
| 11 | 20 | 5 | 5 | 5 |
| 12 | 20 | 5 | 5 | 5 |
| 13 | 20 | 5 | 5 | 5 |
| 15 | 20 | 5 | 5 | 5 |
| 16 | 20 | 5 | 5 | 5 |
| 19 | 20 | 5 | 5 | 5 |
| 20 | 20 | 5 | 5 | 5 |
| 21 | 20 | 5 | 5 | 5 |
| 22 | 20 | 5 | 5 | 5 |
| 23 | 20 | 5 | 5 | 5 |
| 24 | 20 | 5 | 5 | 5 |
| 25 | 20 | 5 | 5 | 5 |
| 26 | 20 | 5 | 5 | 5 |
| 27 | 20 | 5 | 5 | 5 |
| 28 | 20 | 5 | 5 | 5 |
| 29 | 20 | 5 | 5 | 5 |
| 30 | 20 | 5 | 5 | 5 |
| 31 | 20 | 5 | 5 | 5 |
| 32 | 20 | 5 | 5 | 5 |

TABLE 7-continued

| Compound No. | Dosage (g/are) | Herbicidal activity | | |
|---|---|---|---|---|
| | | Japanese millet | Radish | Velvetleaf |
| 33 | 20 | 5 | 5 | 5 |
| 34 | 20 | 5 | 5 | 5 |
| 35 | 20 | 5 | 5 | 5 |
| 36 | 20 | 5 | 5 | 5 |
| 37 | 20 | 5 | 5 | 5 |
| 38 | 20 | 4 | 5 | 5 |
| 39 | 20 | 4 | 5 | 5 |
| 40 | 20 | 5 | 5 | 5 |
| 41 | 20 | 5 | 5 | 5 |
| 42 | 20 | 5 | 5 | 5 |
| 43 | 20 | 5 | 5 | 5 |
| 44 | 20 | 5 | 5 | 5 |
| 45 | 20 | 5 | 5 | 5 |
| 46 | 20 | 5 | 5 | 5 |
| 47 | 20 | 5 | 5 | 5 |

Test Example 3

Cylindrical plastic pots (diameter, 8 cm.; height, 12 cm) were filled with paddy field soil, and the seeds of barnyardgrass (*Echinochloa oryzicola*), broad-leaved weeds (i.e. common falsepimpernel, indian toothcup, waterwort) were sowed in 1 to 2 cm depth. Water was poured therein to make a flooded condition. Buds of arrowhead were sowed in 1 to 2 cm depth, and rice seedlings of the 2.5-leaf stage were transplanted therein, and the test plants were grown in a greenhouse. Six days (at that time weeds began to germinate) thereafter, a designated amount of the test compound formulated in an emulsifiable concentrate according to Formulation Example 2, 3 or 6 and diluted with water (5 ml) was applied to the pots by perfusion. The test plants were grown for an additional 20 days in the greenhouse, and the herbicidal activity was examined. The results are shown in Table 8.

TABLE 8

| Compound No. | Dosage (g/are) | Herbicidal activity | | | |
|---|---|---|---|---|---|
| | | Rice plant | Barnyardgrass | Broad-leaved weed | Arrowhead |
| 3 | 2.5 | — | 5 | 5 | 5 |
| | 0.63 | 0 | 5 | 5 | 5 |
| 5 | 2.5 | — | 5 | 5 | 5 |
| | 0.63 | — | 5 | 5 | 5 |
| 12 | 2.5 | — | 5 | 5 | 5 |
| | 0.63 | 0 | 5 | 5 | 5 |
| 16 | 0.63 | — | 5 | 5 | 5 |
| 27 | 2.5 | — | 5 | 5 | 4 |
| | 0.63 | 1 | 4 | 5 | — |
| 37 | 2.5 | 1 | 5 | 5 | 5 |
| | 0.63 | 1 | 5 | 5 | — |
| 38 | 2.5 | 1 | 4 | 4 | 5 |
| 39 | 2.5 | 1 | 5 | 5 | 5 |
| 44 | 2.5 | 0 | 4 | 4 | 5 |
| A | 2.5 | 0 | 1 | 3 | 1 |
| | 0.63 | 0 | 0 | 1 | 0 |

Test Example 4

Vats (33 cm×23 cm×11 cm) were filled with upland field soil, and the seeds of soybean, peanut, cotton, corn, tall morningglory, velvetleaf, redweed pigweed, black nightshade, common lambsquarters, sicklepod, barnyardgrass (*Echinochloa crus-galli*), johnsongrass and green foxtail were sowed therein to 1 to 2 cm depth. A designated amount of the test compound formulated in an emulsifiable concentrate according to Formulation Example 2, 3 or 6 was diluted with water, and the dilution was sprayed onto the soil surface by means of a small hand sprayer at a spray volume of 10 liters per are. The test plants were further grown in a greenhouse for 20 days, and the herbicidal activity was examined. The results are shown in Table 9.

TABLE 9

| Compound No. | Dosage (g/are) | Soybean | Peanut | Cotton | Corn | Tall morningglory | Velvetleaf | Black nightshade | Redroot pigweed | Common lambsquarters | Sicklepod | Barnyardgrass | Green foxtail | Johnsongrass |
|---|---|---|---|---|---|---|---|---|---|---|---|---|---|---|
| 2 | 2.5 | 0 | 0 | 1 | 1 | 5 | 5 | 4 | 5 | 5 | 4 | 4 | 5 | 5 |
| 3 | 2.5 | 3 | — | 4 | 2 | 5 | 5 | 5 | 5 | 5 | — | 5 | 5 | 5 |
|   | 1.25 | 1 | 0 | 2 | 0 | — | 5 | 5 | 5 | 4 | — | 3 | 4 | 3 |
| 4 | 2.5 | 1 | 0 | 1 | 0 | 5 | 5 | 5 | 5 | 5 | 5 | 4 | 5 | 4 |
| 5 | 2.5 | 0 | 0 | 1 | 0 | 5 | 5 | 5 | 5 | 5 | — | 3 | 5 | 5 |
|   | 1.25 | 0 | 0 | 0 | 0 | 4 | 4 | 4 | 4 | 5 | 3 | — | 3 | 3 |
| 12 | 2.5 | 0 | 0 | 1 | 0 | 5 | 5 | 5 | 5 | 5 | 5 | 5 | 5 | 4 |
|   | 1.25 | 0 | 0 | 0 | 0 | 4 | 5 | 4 | 4 | 5 | 4 | 2 | 4 | 3 |
| 16 | 2.5 | 1 | 0 | 1 | 0 | 5 | 5 | 5 | 5 | 5 | 5 | 5 | 5 | 4 |
|   | 1.25 | 0 | 0 | 0 | 0 | 5 | 4 | 4 | 4 | 5 | 4 | 3 | 5 | 3 |
| 17 | 2.5 | 1 | 0 | 1 | 0 | 5 | 5 | 5 | 5 | 5 | — | 4 | 4 | 4 |
|   | 1.25 | 0 | 0 | 0 | 0 | — | 5 | 5 | 4 | 5 | — | — | — | — |
| 28 | 2.5 | 0 | 0 | 0 | 1 | 5 | 5 | 5 | 5 | 5 | — | 5 | 5 | 5 |
|   | 1.25 | 0 | 0 | 0 | 0 | — | 5 | 5 | 5 | 5 | — | 5 | 5 | 4 |
| 29 | 2.5 | 0 | 0 | 0 | 0 | — | 5 | — | 5 | 5 | 5 | 4 | 4 | 5 |
| 31 | 2.5 | 0 | 0 | 0 | 0 | 5 | 5 | 5 | 5 | 5 | — | 3 | 4 | 5 |
| 37 | 5 | 0 | 0 | — | 0 | 5 | 5 | 5 | 5 | 5 | 5 | 4 | 5 | 4 |
|   | 2.5 | 0 | 0 | 1 | 0 | 5 | 5 | 4 | 5 | 5 | 5 | — | 5 | — |
| 47 | 5 | 0 | 0 | 0 | 0 | — | 5 | 4 | 5 | 5 | — | 4 | 5 | 5 |
|   | 2.5 | 0 | 0 | 0 | 0 | — | 5 | — | 5 | 5 | — | 4 | 5 | 4 |
| A | 5 | 0 | 0 | 0 | 0 | 0 | 3 | 3 | 3 | 3 | 0 | 0 | 0 | 0 |
|   | 2.5 | 0 | 0 | 0 | 0 | 0 | 0 | 0 | 0 | 0 | 0 | 0 | 0 | 0 |

Test Example 5

Vats (33 cm×23 cm×11 cm) were filled with upland field soil, and the seeds of soybean, peanut, cotton, corn, sorghum, tall morningglory, common cocklebur, velvetleaf, sicklepod, black nightshade, prickly sida, hemp sesbania, redroot pigweed, sun spurge, jimsonweed, common lambsquarters, wild mustard, field bindweed, common purslane, fall panicum, large crabgrass, green foxtail, barnyardgrass (*Echinochloa crus-gralli*) and johnsongrass were sowed in 1 to 2 cm depth. A designated amount of the test compound formulated in an emulsifiable concentrate according to Formulation Example 2, 3 or 6 was diluted with water and the dilution was sprayed to the surface of the soil by means of a small hand sprayer at a spray volume of 10 liters per are. The test plants were grown outdoors for 20 days, and the herbicidal activity was examined. The results are shown in Table 10.

TABLE 10

| Weed | Herbicidal activity on Compound No. 16 Dosage (g/are) | |
|---|---|---|
|   | 2.5 | 1.25 |
| Soybean | 1 | 0 |
| Peanut | 1 | 0 |
| Cotton | — | 1 |
| Corn | 1 | 0 |
| Sorghum | — | 1 |
| Tall morningglory | 5 | 5 |
| Common cocklebur | 5 | — |
| Velvetleaf | 5 | 5 |
| Sicklepod | 5 | 4 |
| Black nightshade | 5 | 5 |
| Prickly sida | 5 | 5 |
| Hemp sesbania | 5 | — |
| Redroot pigweed | 5 | 5 |
| Sun spurge | 5 | 5 |
| Jimsonweed | 5 | 5 |
| Common lambsquarters | 5 | 5 |
| Wild mustard | 5 | 5 |
| Field bindweed | 5 | 5 |
| Common purslane | 5 | 5 |
| Fall panicum | 5 | 5 |
| Large crabgrass | 5 | 5 |
| Green foxtail | 5 | 5 |
| Barnyardgrass | 5 | 4 |
| Johnsongrass | 5 | 3 |

Test Example 6

Vats (33 cm×23 cm×11 cm) were filled with upland field soil, and the seeds of wheat, pale smartweed, catchweed bedstraw, common chickweed, persian speedwell and blackgrass were sowed in 1 to 2 cm depth. A designated amount of the test compound formulated in an emulsifiable concentrate according to Formulation Example 2, 3 or 6 was diluted with water, and the dilution was sprayed to the surface of the soil by means of a small hand sprayer at a spray volume of 10 liters per are. The test plants were grown in a greenhouse for 27 days, and the herbicidal activity was examined. The results are shown in Table 11.

TABLE 11

| Compound No. | Dosage (g/are) | Wheat | Pale smartweed | Catchweed bedstraw | Common chickweed | Persian speedwell | Blackgrass |
|---|---|---|---|---|---|---|---|
| 2 | 2.5 | — | 5 | — | 5 | — | 5 |
|   | 1.25 | 1 | 5 | — | 5 | — | — |
| 3 | 2.5 | 0 | 5 | 3 | 5 | 5 | 4 |
|   | 1.25 | 0 | 5 | — | 5 | 4 | 3 |
| 4 | 2.5 | 1 | 5 | — | 5 | 5 | 3 |
|   | 1.25 | 1 | 5 | — | 5 | 3 | — |
| 5 | 2.5 | — | 5 | 5 | 5 | 5 | 5 |
|   | 1.25 | 0 | 5 | 4 | 5 | 5 | 3 |

TABLE 11-continued

| Compound No. | Dosage (g/are) | Herbicidal activity | | | | | |
|---|---|---|---|---|---|---|---|
| | | Wheat | Pale smartweed | Catchweed bedstraw | Common chickweed | Persian speedwell | Blackgrass |
| 12 | 2.5 | 1 | 5 | 5 | 5 | 5 | 3 |
| | 1.25 | 0 | 5 | 5 | 5 | 5 | — |
| 16 | 2.5 | 1 | 5 | — | 5 | 5 | 4 |
| | 1.25 | — | 5 | — | 5 | 5 | 3 |
| 17 | 2.5 | — | 5 | 5 | 5 | 5 | 5 |
| | 1.25 | 0 | 5 | 5 | 5 | 5 | 4 |
| 18 | 2.5 | — | 5 | 5 | 5 | 5 | 3 |
| 27 | 2.5 | 1 | — | 5 | — | 5 | — |
| 28 | 2.5 | — | 5 | 5 | 5 | 5 | 5 |
| | 1.25 | 1 | 5 | 3 | 5 | 5 | 5 |
| 29 | 2.5 | 1 | 5 | 3 | 5 | 5 | 4 |
| | 1.25 | 0 | 5 | — | 5 | 3 | — |
| 31 | 2.5 | — | 5 | 5 | 5 | 5 | 5 |
| | 1.25 | 1 | 5 | — | 5 | 4 | 4 |
| 37 | 2.5 | 1 | — | 3 | 5 | 5 | — |
| A | 2.5 | 0 | 0 | 0 | 0 | 0 | 0 |
| | 1.25 | 0 | 0 | 0 | 0 | 0 | 0 |

Test Example 7

Vats (33 cm×23 cm×11 cm) were filled with upland field soil, and the seeds of corn, common cocklebur, velvetleaf, tall morningglory, black nightshade and redroot pigweed were sowed therein and cultivated for 18 days in a greenhouse. A designated amount of the test compound formulated in an emulsifiable concentrate according to Formulation Exxample 2, 3 or 6 was diluted with water containing a spreading agent, and the dilution was sprayed over the foliage of the test plants by means of a small hand sprayer at a spray volume of 5 liters per are. The test plants were further grown in the greenhouse for 20 days, and the herbicidal activity was examined. At the time of the application, the test plants were generally at the 1 to 4 leaf stage and in 2 to 12 cm height, although growing stage of the test plants varied depending on their species. The results are shown in Table 12.

TABLE 12

| Compound No. | Dosage (g/are) | Herbicidal activity | | | | | |
|---|---|---|---|---|---|---|---|
| | | Corn | Tall morningglory | Common cocklebur | Velvetleaf | Black nightshade | Redroot pigweed |
| 2 | 0.1 | 0 | 5 | — | 5 | 5 | 5 |
| 3 | 0.1 | — | 5 | 5 | 5 | 5 | 5 |
| 4 | 0.1 | — | 5 | 5 | 5 | 5 | 5 |
| 5 | 0.1 | 1 | 5 | 5 | 5 | 5 | 5 |
| 12 | 0.1 | 0 | 5 | 5 | 5 | 5 | 5 |
| 16 | 0.1 | 1 | 5 | 5 | 5 | 5 | 5 |
| 27 | 0.1 | — | 5 | 5 | 5 | 5 | 5 |
| 28 | 0.1 | — | 5 | 5 | 5 | 5 | 5 |
| 29 | 0.1 | 0 | — | 5 | 5 | 5 | 5 |
| 31 | 0.1 | 1 | 5 | 5 | 5 | 5 | 5 |
| 37 | 0.1 | 1 | 5 | 4 | 4 | 5 | 5 |
| 39 | 0.3 | 1 | 5 | — | 5 | 5 | 5 |
| | 0.1 | 0 | 5 | — | 5 | 5 | 5 |
| 44 | 0.3 | — | 5 | 4 | 5 | 5 | 5 |
| | 0.1 | 1 | 5 | — | 4 | 5 | 5 |
| 45 | 0.3 | 1 | 5 | — | 4 | 5 | 5 |
| | 0.1 | 0 | 5 | — | — | 4 | 4 |
| 47 | 0.3 | 1 | 5 | — | 4 | 4 | 4 |
| A | 0.3 | 0 | 0 | 0 | 0 | 0 | 0 |
| | 0.1 | 0 | 0 | 0 | 0 | 0 | 0 |

Test Example 8

Vats (33 cm×23 cm×11 cm) were filled with upland field soil, and the seeds of wheat, ladysthumb, catchweed bedstraw, common chickweed and persian speedwell were sowed therein and cultivated for 18 days in a greenhouse. A designated amount of the test compound formulated in an emulsifiable concentrate according to Formulation Example 2, 3 or 6 was diluted with water containing a spreading agent, and the dilution was sprayed over the foliage of the test plants by means of a small hand sprayer at a spray volume of 5 liters per are. The test plants were further grown in the greenhouse for 20 days, and the herbicidal activity was examined. At the time of the application, the test plants were generally at the 1 to 4 leaf stage and in 2 to 12 cm height, although the growing stage of the test plants varied depending on their species. The results are shown in Table 13.

TABLE 13

| Compound No. | Dosage (g/are) | Herbicidal activity | | | | |
|---|---|---|---|---|---|---|
| | | Wheat | Ladysthumb | Catchweed bedstraw | Common chickweed | Persian speedwell |
| 3 | 0.1 | — | 5 | 5 | 5 | 5 |
| 4 | 0.1 | 1 | 5 | 5 | 5 | 5 |
| 5 | 0.1 | 1 | 5 | 5 | 5 | 5 |
| 12 | 0.1 | — | 5 | 5 | 5 | 5 |
| 16 | 0.1 | 1 | 5 | 5 | 5 | 5 |
| 34 | 0.3 | 1 | 5 | 5 | 4 | 5 |
| | 0.1 | 1 | 5 | 4 | — | 4 |
| 42 | 0.3 | 1 | 5 | 4 | — | 5 |
| | 0.1 | 1 | 4 | — | — | 5 |
| A | 0.3 | 0 | 0 | 0 | 0 | 0 |

Test Example 9

Seeds of corn, velvetleaf, redroot pigweed and black nightshade were sowed in the field as previously laid up in ridges and divided into plots of 3 m². A designated amount of the test compound formulated into an emulsifiable concentrate according to Formulation Example 2 or 5 was diluted with water, and the dilution was sprayed onto the soil surface by means of a small hand sprayer at a spray volume of 10 liters per are. The application was made with three repetitions. After cultivation for 32 days, the herbicidal activity was examined. The results are shown in Table 14.

TABLE 13-continued

| Compound No. | Dosage (g/are) | Herbicidal activity ||||| 
|---|---|---|---|---|---|---|
| | | Wheat | Ladys-thumb | Catchweed bedstraw | Common chickweed | Persian speedwell |
| | 0.1 | 0 | 0 | 0 | 0 | 0 |

TABLE 14

| Compound No. | Dosage (g/are) | Herbicidal activity ||||
|---|---|---|---|---|---|
| | | Corn | Velvetleaf | Redroot pigweed | Black nightshade |
| 5 | 1.6 | 0 | 5 | 5 | 5 |
| | 0.8 | 0 | 5 | 5 | 5 |
| 16 | 1.6 | 0 | 5 | 5 | 5 |
| | 0.8 | 0 | 5 | 5 | 5 |
| B | 8 | 0 | 2 | 1 | 5 |
| | 4 | 0 | 1 | 1 | 4 |

What is claimed is:

1. A compound of the formula:

wherein R is a hydrogen atom, a $C_1$–$C_5$ alkyl group, a $C_3$–$C_4$ alkenyl group, a $C_3$–$C_4$ alkynyl group, a halo($C_1$–$C_4$)alkyl group, a halo($C_3$–$C_4$)alkenyl group, a halo($C_3$–$C_4$)alkynyl group, a $C_1$–$C_2$ alkoxy($C_1$–$C_2$)alkyl group, a $C_1$–$C_2$ alkoxy($C_1$–$C_2$)alkoxy($C_1$–$C_2$)alkyl group, a cinnamyl group, a cyano($C_1$–$C_3$)alkyl group, a carboxy($C_1$–$C_3$)alkyl group, a $C_1$–$C_5$ alkoxycarbonyl($C_1$–$C_3$)alkyl group, a halo($C_1$–$C_5$)alkoxycarbonyl($C_1$–$C_3$)alkyl group, a $C_1$–$C_2$ alkoxy($C_1$–$C_2$)alkoxycarbonyl($C_1$–$C_3$)alkyl group, a $C_1$–$C_5$ alkoxycarbonyl($C_1$–$C_2$)alkoxycarbonyl($C_1$–$C_3$)alkyl group,, a cyclo($C_3$–$C_6$)alkoxycarbonyl($C_1$–$C_3$)alkyl group, a $C_1$–$C_5$ alkylaminocarbonyl($C_1$–$C_3$)alkyl group or a di($C_1$–$C_5$)alkylaminocarbonyl($C_1$–$C_3$)alkyl group.

2. The compound according to claim 1, wherein R is a $C_1$–$C_5$ alkyl group, a $C_3$–$C_4$ alkenyl group, a $C_3$–$C_4$ alkynyl group, a halo($C_1$–$C_4$)alkyl group, a halo($C_3$–$C_4$)alkenyl group, a halo($C_3$–$C_4$)alkynyl group, a $C_1$–$C_2$ alkoxy($C_1$–$C_2$)alkyl group or a $C_1$–$C_2$ alkoxy($C_1$–$C_2$)alkyl group.

3. The compound according to claim 2, wherein R is a $C_2$–$C_4$ alkyl group, a $C_3$–$C_4$ alkenyl group, a $C_3$–$C_4$ alkynyl group or a halopropynyl group.

4. The compound according to claim 3, wherein R is a $C_2$–$C_3$ alkyl group, a $C_3$–$C_4$ alkenyl group or a $C_3$–$C_4$ alkynyl group.

5. The compound according to claim 4, which is 2-[6-fluoro-3-(1-methylethyl)-2(3H)-benzothiazolon-5-yl]-4,5,6,7-tetrahydro-2H-isoindole-1,3-dione.

6. The compound according to claim 4, which is 2-[6-fluoro-3-(2-propenyl)-2(3H)-benzothiazolon-5-yl]-4,5,6,7-tetrahydro-2H-isoindole-1,3-dione.

7. The compound according to claim 4, which is 2-[6-fluoro-3-(2-propynyl)-2(3H)-benzothiazolon-5-yl]-4,5,6,7-tetrahydro-2H-isoindole-1,3-dione.

8. A herbicidal composition which comprises a herbicidally effective amount of the compound according to claim 1 and an inert carrier or diluent.

9. A method for controlling the growth of undesired weeds, which comprises applying a herbicidally effective amount of the compound according to claim 1 and an inert carrier or diluent to the area where the undesired weeds grow or will grow.

10. The method according to claim 9, wherein the area is a corn or sorghum field.

* * * * *